United States Patent [19]
Loeffler

[11] Patent Number: 5,701,914
[45] Date of Patent: Dec. 30, 1997

[54] MALE CONTRACEPTIVE

[76] Inventor: Charles P. Loeffler, 5573 Peacock La., Riverside, Calif. 92505

[21] Appl. No.: 550,954

[22] Filed: Oct. 31, 1995

[51] Int. Cl.$^6$ .................................................. A61F 6/02
[52] U.S. Cl. ................................. 128/842; 128/843
[58] Field of Search ........................... 128/842–844, 128/918, 885; 604/347–353; 600/29–31

[56] References Cited

U.S. PATENT DOCUMENTS

| | | |
|---|---|---|
| 2,649,854 | 8/1953 | Salm . |
| 2,696,209 | 12/1954 | Varaney . |
| 3,332,312 | 7/1967 | Bixby . |
| 3,373,746 | 3/1968 | White et al. . |
| 3,463,141 | 8/1969 | Mozolf . |
| 3,648,683 | 3/1972 | Brodie ............................ 128/843 |
| 3,704,704 | 12/1972 | Gonzalas ...................... 128/843 |
| 3,746,218 | 7/1973 | Risdon et al. . |
| 3,880,137 | 4/1975 | Bucalo ........................... 128/843 |
| 3,951,132 | 4/1976 | Bucalo ........................... 128/843 |
| 4,139,007 | 2/1979 | Diamond . |
| 4,258,947 | 3/1981 | Thompson et al. . |
| 4,457,299 | 7/1984 | Cornwell . |
| 4,503,879 | 3/1985 | Lazarus . |
| 4,682,592 | 7/1987 | Thorsgard . |
| 4,771,810 | 9/1988 | Ermold et al. . |
| 4,821,742 | 4/1989 | Phelps, III . |
| 4,869,241 | 9/1989 | Friedmann . |

Primary Examiner—Michael A. Brown
Attorney, Agent, or Firm—Sheldon & Mak

[57] ABSTRACT

A contraceptive device for blocking a male urethra canal includes an expandable body unit having an elastic member covering a plurality of body segments, a forwardly opening cavity extending within the body unit and having first, second, and third progressively rearwardly spaced cavity regions collectively in the body segments, a cam member having an expansion cam and a forwardly extending shaft being movable in the cavity with the cam sequentially locatable in the first, second, and third regions thereof, for expanding the body unit from a contracted configuration for insertion into a male urethra penis cavity to an expanded configuration 10% or more larger than the contracted position for blocking the urethra when the cam is in the second region, the body contracting to the contracted configuration for permitting withdrawal of the body unit when the cam is in the third region, the cam member being blocked from moving from the second position to the first position and from the third position to the second position for preventing successive uses of the device, and a cam actuator having an expanding position and a contracting position on the shank of the cam member and a handle portion projecting forwardly of the body unit for manipulating the device, the cam member being blocked from the third position when the actuator is in the expanding position, the first position of the cam member being visually distinguishable from the other positions thereof externally of the device.

10 Claims, 4 Drawing Sheets

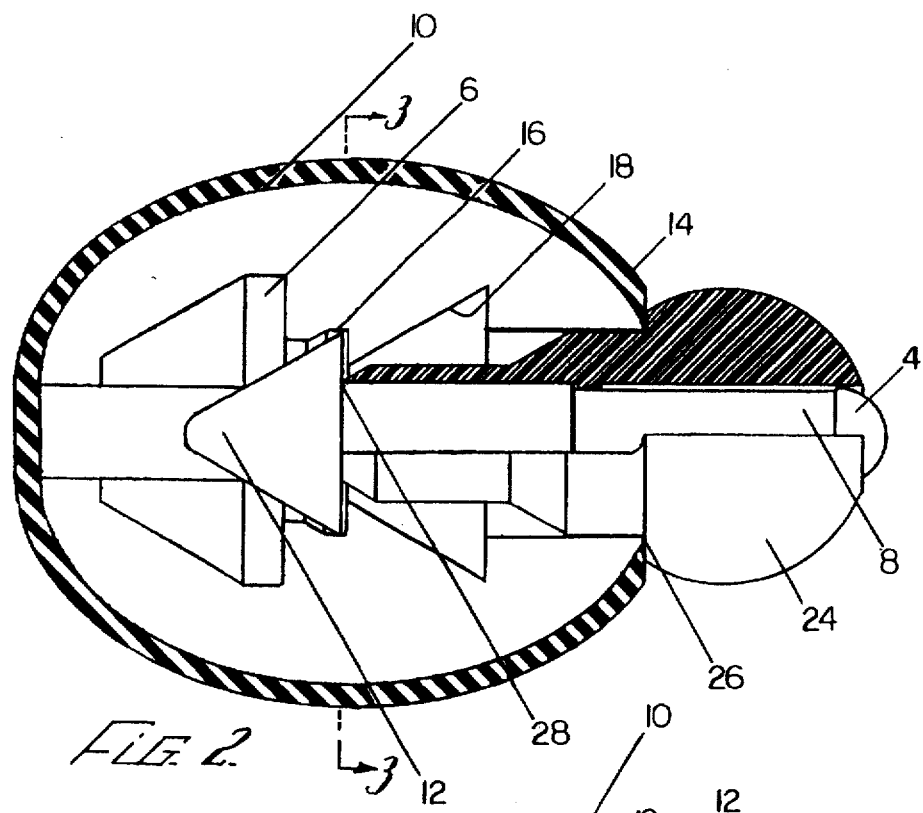
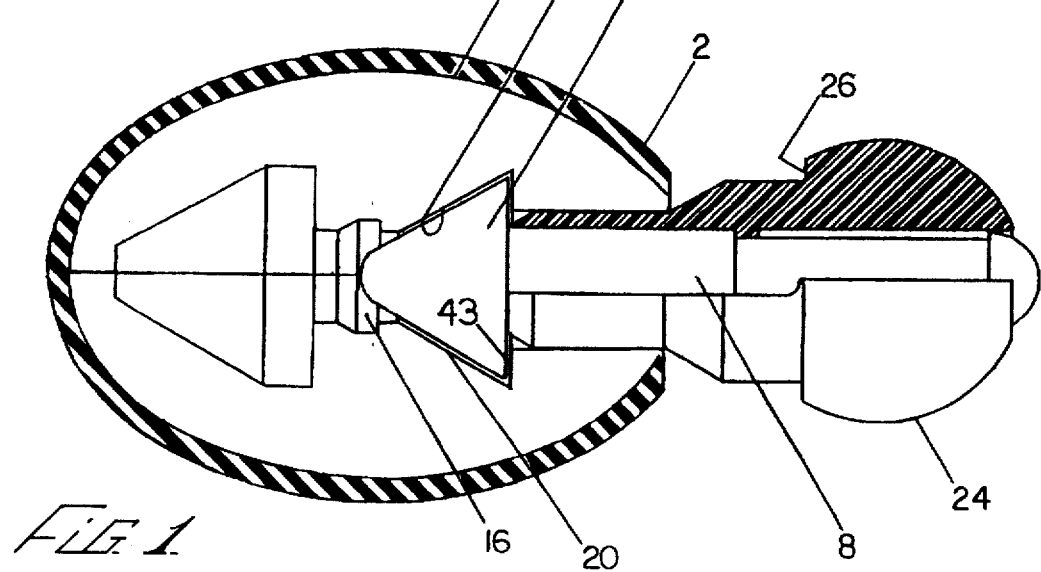

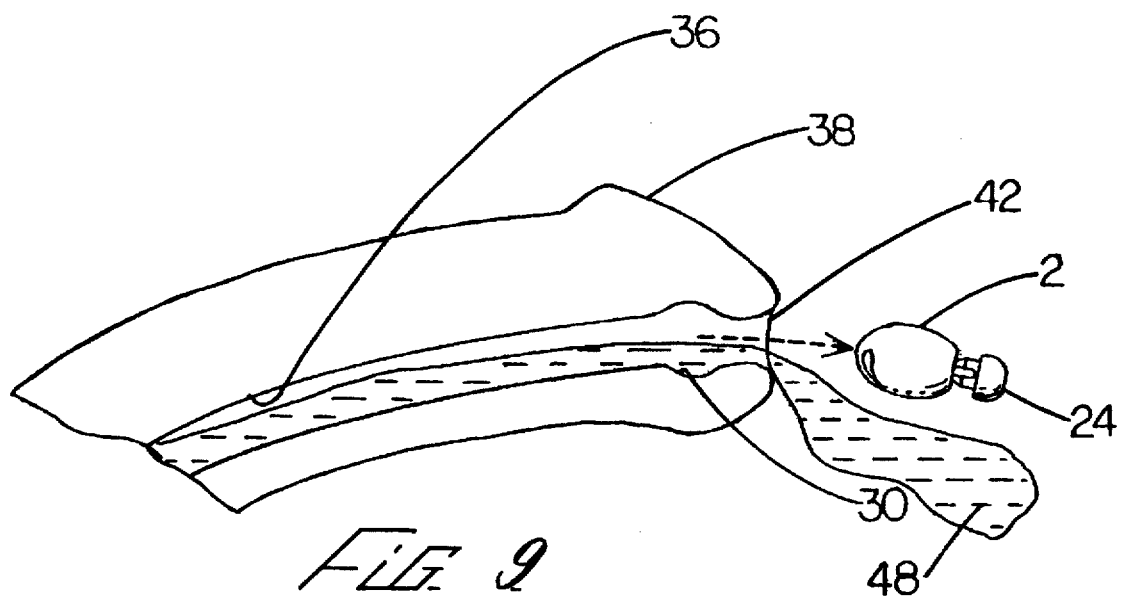
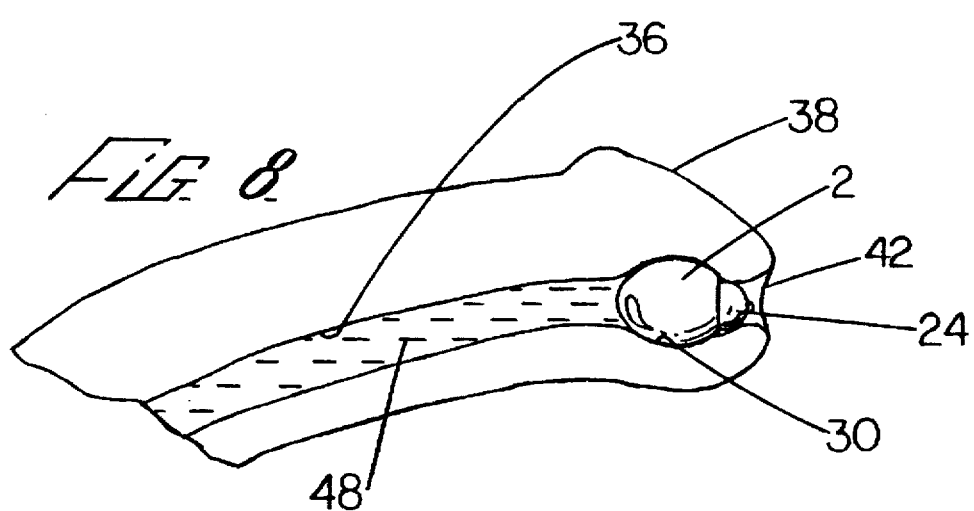

MALE CONTRACEPTIVE

BACKGROUND

The present invention relates to male contraceptive devices, and more particularly to male contraceptive devices that do not require surgical intervention.

The most common male contraceptive device, the condom, has at least three major drawbacks. The use thereof requires a physical response on the part of the male partner in order to be worn. This use often compromises the passion in a sexual act, postponing culmination by the necessity of wearing the prophylactic in order to prevent unwanted pregnancy. Secondly, the material used in these devices becomes a barrier between the partners, reducing vital sensitivity during intercourse. Thirdly, failure of the material composing the prophylactic, or accidental removal, causes known high failure rates of about 32%, often resulting in unwanted pregnancy and/or further increasing the risk of sexually transmitted diseases.

U.S. Pat. No. 2,696,209 to Varaney discloses an internal contraceptive device in the form of a rigid tubular member that is covered by a flexible sack that can be folded back inside of itself, the open end of the tubular member is inserted into the urethra and moved along by finger pressure on the outside of the penis, and the bag is also moved into the urethra, by means such as another tube and a plunger. This device is substantially awkward to use, and is somewhat complex, having a number of separate parts to be managed. U.S. Pat. No. 3,373,746 to White et al. discloses encapsulated foam members and having a spermacide to produce a chemical congealing action with semen for sealing to prevent conception. U.S. Pat. No. 4,139,007 to Diamond discloses an external device that seals off the urethra. The disadvantages to this device include a hard external band that may cause pain and chaffing to the vagina and also may be of marginal safety as far as prevention of pregnancy if it is not adjusted properly. U.S. Pat. No. 4,821,742 to Phelps, III discloses an external device only, and U.S. Pat. No. 4,457,299 to Cornwell discloses an internal device that seals the urethra against low pressure to prevent incontinence but does not seal against higher pressures associated with intentional evacuation; there is no disclosure of a contraceptive device. It is believed that in addition to the above disadvantages, several of the devices are ineffective against external fluid entering the urethra, and none of the prior art devices prevents the unsafe practice of reusing the device, which reuse creates the risk of contamination from person to person.

Thus there is a need for a male contraceptive that does not require surgery, can only be used one time, and is simple to use and install.

SUMMARY

The present invention meets this need by providing an internally worn male contraceptive device that positively locks to block the urethra, and that once unlocked cannot again be locked, thereby preventing hazardous subsequent uses. In one aspect of the invention, the device includes an expandable body unit having a forwardly opening body cavity, a cam member being movable for successively engaging first, second and third regions of the cavity, but not in reverse sequence, and expanding the body unit from a contracted condition in the first region to an expanded position in the second region, then returning the body unit to the contracted condition in the third region of the cavity.

Preferably the device further includes a cam actuator projecting on a shank of the cam member from the body unit and having expanding and contracting positions relative to the cam member, the actuator in the expanding position blocking the cam member from the third region of the cavity for preventing premature contraction of the body unit during or following insertion and expansion of the device. The blocking from the third region can be effected by a stop face of the actuator engaging the body unit as the cam member reaches the second region of the cavity. The actuator can engage a forwardly facing shoulder of the shank to hold the actuator in the contracting position during movement of the cam member to the third region of the cavity. Preferably the presence of the cam member in the first cavity region is visually distinguishable from the other positions externally of the device.

The body unit can have a plurality of body segments spaced about the cam member and an elastic covering over the segments. The cavity including each of the regions is formed collectively in portions of all of the body segments, the elastic covering urging the segments into engagement with the cam member and sealingly blocking the urethra when the body unit is in the penis cavity in the expanded configuration.

Preferably the device expands from a contracted outside diameter D to an expanded diameter D' that is lat least about 10 percent larger than D for holding the body unit sealingly engaged with the penis cavity. More preferably, D' is at least about 14 percent greater than D. The body unit can have a smooth, elongate shape that is approximately elliptical in lingitudinal cross-section for facilitating insertion into the urethral canal.

DRAWINGS

These and other features, aspects, and advantages of the present invention will become better understood with reference to the following description, appended claims, and accompanying drawings, where:

FIG. 1 is a lateral sectional view of a male contraceptive device according to the present invention, the device being in a pre-insertion contracted condition;

FIG. 2 is a lateral sectional view of the device of FIG. 1 in an expanded condition;

FIG. 8 is a partial sectional view of FIG. 7 showing the device in the expanded condition of FIG. 2; and FIG. 9 is a partial sectional view as in FIG. 7 showing the device in the contracted condition of FIG. 5 being removed from the penis cavity.

DESCRIPTION

Figure 4:
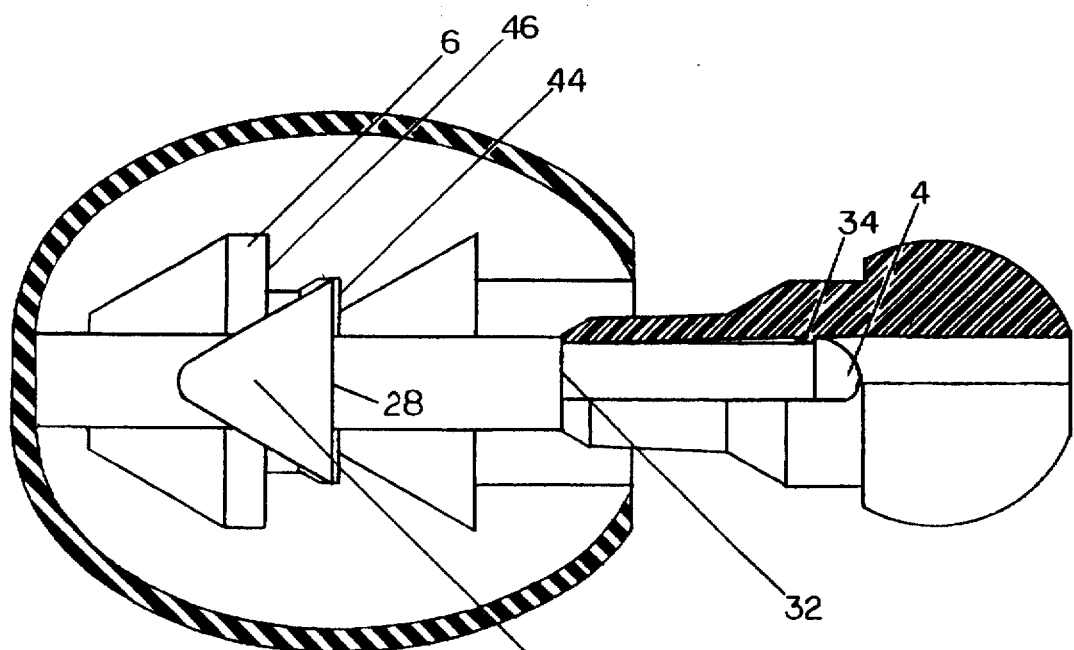
FIG. 4 is lateral sectional view of the device of FIG. 1 in an extended condition.

The present invention is directed to a male contraceptive that does not fail due to friction, prevents transfer of body fluids, causes no loss of sensitivity between partners, and does not require an erection of the penis prior to and during use. With reference to FIGS. 1–6 of the drawings, a contraceptive device 2 includes an expansion cam 12 having a forwardly facing cam face 28, the cam 12 being centrally located relative to a plurality of wedge-shaped body segments 10 that are arranged circularly around the cam 12. A fluid-impervious elastic covering 14 surrounds the body segments 10, biasingly holding the body segments 10 in proximity to the expansion cam 12.

Figure 6:
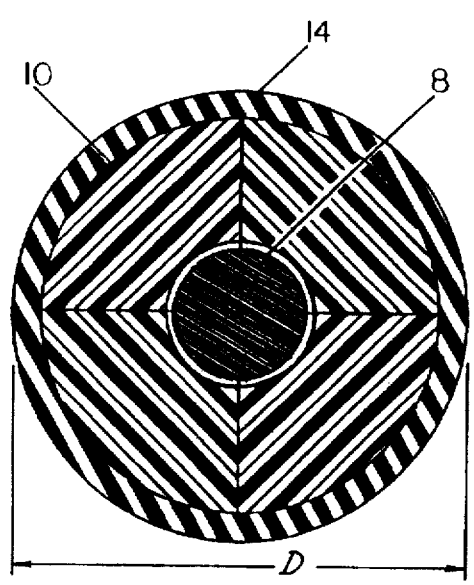
FIG. 6 is a sectional view of the device of FIG. 1 on line 6—6 of FIG. 5.
Figure 3:
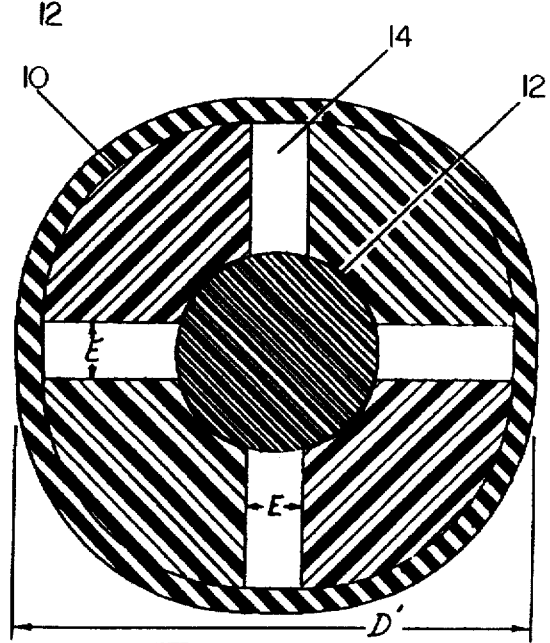
FIG. 3 is a sectional view of the device of FIG. 1 on line 3—3 of FIG. 2.

The combination of the body segments 10 and the elastic covering 14 provides a body unit that is expandable from a contracted configuration of approximately elliptical longitudinal cross-section as shown in FIG. 1 and approximately circular cross-sectional outline having an outside diameter D as shown in FIG. 6, to an expanded configuration as shown in FIGS. 2 and 3. The expanded configuration has an enlarged expansion diameter D' by virtue of the body segments 10 moving apart by an expansion distance E in response to rearward movement of the expansion cam 12 from a pre-expansion cavity 18 to an expansion cavity 16, the cavities 16 and 18 being formed in part in each of the body segments 10. Further rearward movement of the expansion cam 12 into a contraction cavity 6 causes the body segments 10 return to an abutting relationship in response to contraction of the elastic covering 14. Forward movement of the expansion cam 12 from the contraction cavity 6 is blocked by engagement of the cam face 28 with a contraction cavity face 46 that is collectively formed in the body segments 10 at a forward extremity of the contraction cavity 6. Similarly, forward movement of the cam 12 from the expansion cavity 16 is blocked by an expansion cavity face 44 that is formed at a forward extremity of the expansion cavity 16; likewise, a pre-expansion cavity face 43 blocks forward movement of the cam 12 from the pre-expansion cavity The expansion cam 12 has a cam shaft 8 rigidly extending forwardly therefrom, and a cam actuating member 24 is moveably attached to the cam shaft 8 for manipulating the device 2, the actuating member 24 extending outside of the elastic member 14. The cam actuating member 24 is formed with a cam actuating stop face 26 that can contact the front extremities of the body segments 10, thereby limiting rearward movement of the expansion cam 12 under certain conditions as descibed below. The actuating member 24 is also formed with a retaining shoulder 34, and the cam shaft 8 is formed with a retaining boss 4 and a cam shaft shoulder 32 that is spaced between the boss 4 and the cam face 28 as shown in FIG. 4, the shoulder 34 being movable between the cam shaft shoulder 32 and the boss 4. Further, the actuating member 24 is formed with a plurality of rearwardly opening flex slots 40, the rear extremity of the member 24 being biased inwardly against the cam shaft 8 during forward movement thereof relative to the cam shaft 8 until the retaining shoulder 34 is proximate the boss 4, at which point the rear of the member 24 locks into engagement with the cam shaft shoulder 32. Thus the shoulder 32, together with the boss 4 and the cam face 28, limit axial movement of the actuating member 24 relative to the expansion cam 12. Accordingly, the actuating member 24 initially contacts the cam face 28 for moving the cam 12 from the pre-expansion cavity 18 as shown in FIG. 1 to the expansion cavity 16 as shown in FIG. 2, the stop face 26 then contacting the body segments 10 for preventing further rearward movement of the cam 12 relative to the body segments 12.

In moving into the expansion cavity 16, the cam 12 effects expansion of the device from the contracted condition to the expanded condition by the expansion cavity 16 being smaller than the pre-expansion cavity 18. This size differential is substantially maintained in each condition of expansion and contraction. The expansion is facilitated by the pre-expansion cavity 18 being formed conically at a body expansion angle as indicated at 20, the expansion cam 12 being conically formed at a corresponding angle for ramping the body segments 10 outwardly as the cam 12 moves rearwardly. The body segments 10 are maintained in alignment during the expansion by the cam 12 being conically shaped corresponding to the body expansion angle 20 of the pre-expansion cavity 18, and by the expansion cavity 16 extending rearwardly of a center of radial pressure between the body segments 10 and the elastic covering 14, the rearward portion of the expansion cavity also being conically shaped corresponding to the expansion angle 20 for engaging an outer portion of the expansion cam 12. Further, a portion of the actuator member 24 extending rearwardly of the stop face 26 is conically shaped corresponding to the expansion angle 20 and proportioned for expanding rear extremities of the body segments 10 in unison with operation of the expansion cam 12 rearwardly from the pre-expansion cavity 18.

Figure 5:
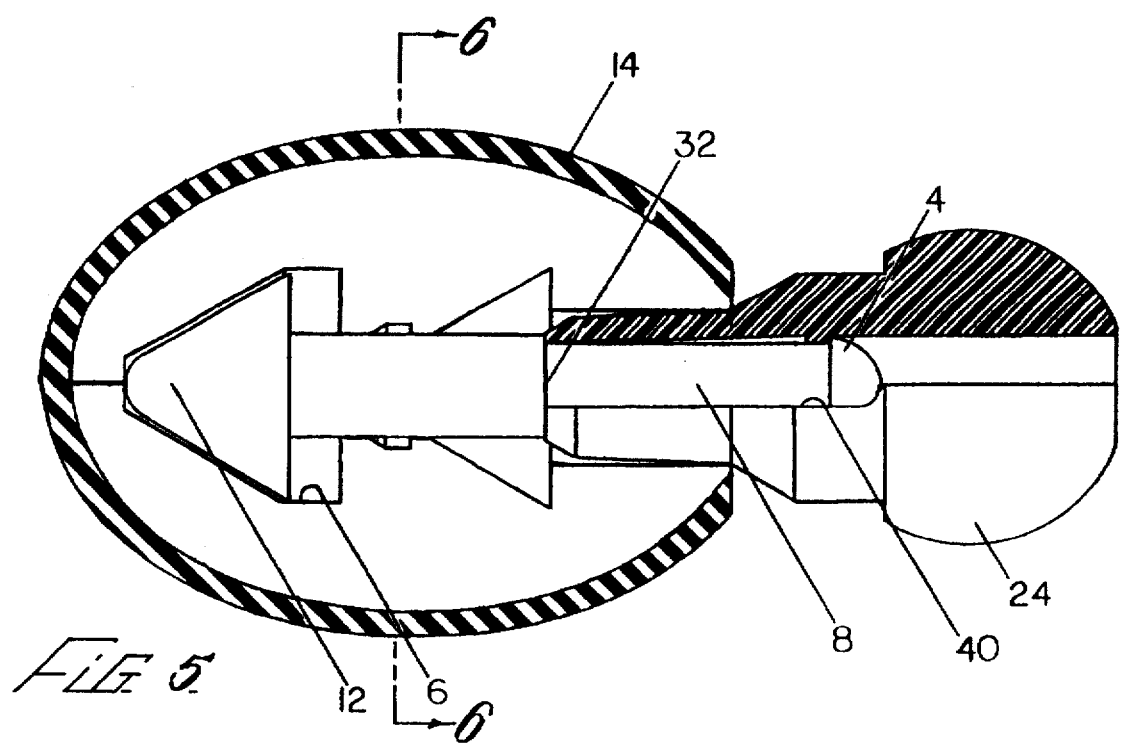
FIG. 5 is a lateral sectional view of the device of FIG. 1 in a post-expanded contracted condition.

Further movement of the expansion cam 12 into the contraction cavity 6 is made possible by first moving the cam actuating member 24 forwardly on the cam shaft 8 until the retaining shoulder 34 is proximate the retaining boss 4 as shown in FIG. 4, the rear of the member 24 being locked onto the shaft shoulder 32 as described above. Then, the final contracted condition is achieved by moving the actuator member 24 together with the expansion cam 12 rearwardly relative to the segment members 10 until the cam 12 snaps into the contraction cavity 6, the contraction cavity 6 being larger than the cam 12. Further movement of the expansion cam rearwardly of the contraction cavity 6 is prevented by suitable means, such as the front extremity of the cavity 6 being formed perpendicular to the direction of travel of the expansion cam 12 as shown in FIG. 5, the body segments 10 thereat being in facing contact in the contracted condition.

Figure 7:
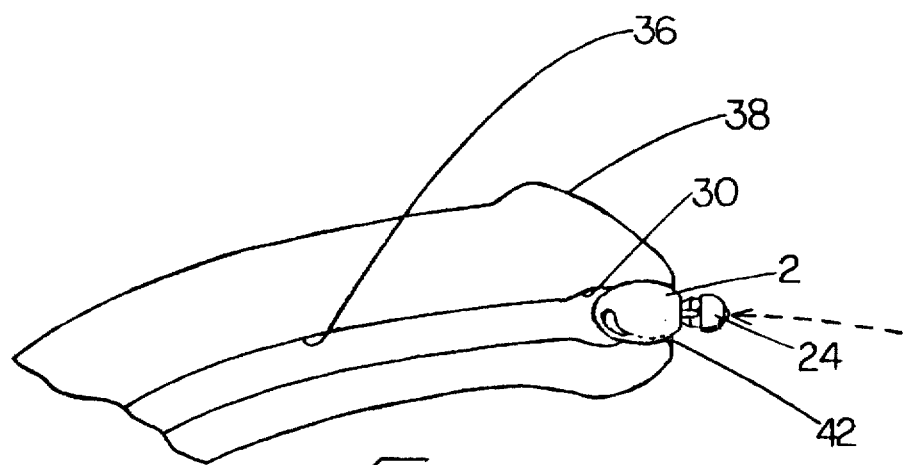
FIG. 7 is a lateral partial sectional view showing the device of FIG. 1 being inserted into a penis cavity.

In use, and with further reference to FIGS. 7-9, the male contraceptive device 2 is inserted in a penis 38 through a urethra canal opening 42 as shown in FIG. 7, being positioned with the combination of the body segments 10 and the elastic covering 14 seated in a natural penis cavity 30 that is located in the head of the penis 38. For this purpose, the diameter D is preferred to be between approximately 0.37 inch and approximately 0.42 inch. Movement of the device 2 into the penis cavity 30 is facilitated by manipulating the externally extending cam actuating member 24, the expansion cam 12 being initially located in the pre-expansion body cavity 18 as described above in connection with FIG. 1. The cam actuating member 24 is then pushed rearwardly relative to the body segments 10 for forcing the expansion cam 12 from the pre-expansion cavity 18 and into the expansion cavity 16 as described above in connection with FIG. 2, thereby expanding the male contraceptive device 2 to the expansion diameter D' for preventing the discharge of seminal fluid 48 from the penis 38 as shown in FIG. 8. It is preferred that the expansion diameter D' be at least approximately 10 percent greater than the diameter D, 0.407 inch in the case of D being 0.37 inch. More preferably, the expansion diameter D' is at least 14 percent greater than D, approximately 0.422 inch in this example. Aside from physical limitations with the structure of the device 10, the upper limit of the expansion diameter D' relates only to the onset of discomfort in use. This operation can be facilitated by forward finger pressure rearwardly of the penis cavity 30. Further rearward travel of the cam 12 is prevented by the stop face 26 of the actuating member 24 contacting the body segments 10 as described above. The contraceptive device 2 is now expanded to block the urethra canal opening 42 thus preventing the discharge of semen from the penis 38. The urethra canal 36 is sufficiently long to provide a temporary reservoir for the seminal fluid 48.

Removal of the contraceptive device 2 from the penis 38 requires pulling the cam actuating member 24 forward to engage the cam shaft shoulder 32 as described above relative to FIG. 4. When locked in this new position, pushing the cam actuating member 24 rearwardly relative to the body segments 10 moves the expansion cam 12 into the contraction cavity 6 as described relative to FIG. 5, the device 2 being removed by pulling on the actuator 24 as shown in FIG. 9.

Thus the device 2 of the present invention provides an internally worn male contraceptive that cannot be used more than once. Prior use of the device 2 is immediately visually discernable by observation of the position of the cam shaft retaining boss 4 being displaced within the actuator 24 as shown in FIG. 5. The device 2, being worn internally, does not result in a loss of sensitivity during intercourse, and it can be inserted and worn both prior to or subsequent to erection. The elastic covering 14 being impervious to the seminal fluid 48, in combination with the body segments 10 being locked in the expanded condition by the cam 12, provides positive blockage of the urethra canal 36.

Although the present invention has been described in considerable detail with reference to certain preferred versions thereof, other versions are possible. For example, different numbers of the body segments, appropriately configured can be substituted for the four segments 10 that are depicted in FIGS. 3 and 6. Also, the elastic covering 14 can be formed integrally with the body segments 10. Therefore, the spirit and scope of the appended claims should not necessarily be limited to the description of the preferred versions contained herein.

What is claimed is:

1. A contraceptive device for blocking a male urethra canal having a canal opening and a penis cavity, the device comprising:

(a) an expandable body unit, a forwardly opening cavity extending longitudinally within the body unit and having first, second, and third cavity regions formed therein, the first region being located forwardly of the third region, the second region being spaced between the first and third regions; and (b) a cam member having an expansion cam and a forwardly extending shaft, the cam member being movable in the cavity with the cam being sequentially locatable in the first, second, and third regions thereof, the cam cooperating with the cavity for expanding the body unit from a contracted configuration for permitting insertion of the body unit into the penis cavity to an expanded configuration for blocking the urethra when the cam is moved from the first region to the second region, the body contracting to the contracted configuration for permitting withdrawal of the body unit when the cam is moved from the second region to the third region, the cam member being blocked from moving from the second position to the first position and from the third position to the second position for preventing successive uses of the device.

2. The device of claim 1, further comprising a cam actuator connected to the shank of the cam member and having a handle portion projecting forwardly of the body unit for manipulating the device, the actuator being movable relative to the cam member from an expanding position to a contracting position, the cam member being movable from the first postion to the second position, but not the third position, when the actuator is in the expanding position, the cam member being movable from the second position to the third position when the actuator is in the contracting position.

3. The device of claim 2, wherein the actuator has a stop face formed thereon, the stop face contacting the body unit for preventing movement of the cam member to the third position when the cam member is in the second position and the actuator is in the expanding position.

4. The device of claim 2, wherein the shank of the cam member has a forwardly facing shoulder formed thereon, the actuator engaging the shoulder for holding the actuator in the contracting position when the cam member is being moved by the actuator to the third position.

5. The device of claim 2, wherein the first position of the cam member is visually distinguishable from the other positions thereof externally of the device.

6. The device of claim 1, wherein the body unit comprises:

(a) a plurality of body segments, the body segments being angularly spaced about the cam member and having respective portions of the cavity formed therein; and (b) an elastic covering extending about the body segments, the covering biasingly holding the segments in engagement with the cam member and sealingly blocking the urethra when the body unit is located in the penis cavity in the expanded configuration.

7. The device of claim 1, wherein the body unit has an outside diameter D in the contracted condition and an expansion diameter D' in the expanded condition, D' being at least approximately 10 percent larger than D for holding the body unit sealingly engaged with the penis cavity.

8. The device of claim 7, wherein D' is at least approximately 14 percent greater than D.

9. The device of claim 1, wherein the body unit is approximately elliptical in longitudinal cross-section.

10. A contraceptive device for blocking a male urethra canal having a canal opening and a penis cavity, the device comprising:

(a) an expandable body unit, a forwardly opening cavity extending longitudinally within the body unit and having first, second, and third cavity regions formed therein, the first region being located forwardly of the third region, the second region being spaced between the first and third regions, the body unit comprising:

(i) a plurality of body segments, the body segments being angularly spaced about the cam member and having respective portions of the cavity formed therein; and (ii) an elastic covering extending about the body segments, the covering biasingly holding the segments in engagement with the cam member and sealingly blocking the urethra when the body unit is located in the penis cavity in the expanded configuration;

(b) a cam member having an expansion cam and a forwardly extending shaft, the cam member being movable in the cavity with the cam being sequentially locatable in the first, second, and third regions thereof, the cam cooperating with the cavity for expanding the body unit from a contracted configuration for permitting insertion of the body unit into the penis cavity to an expanded configuration for blocking the urethra when the cam is moved from the first region to the second region, the body contracting to the contracted configuration for permitting withdrawal of the body unit when the cam is moved from the second region to the third region, the cam member being blocked from moving from the second position to the first position and from the third position to the second position for preventing successive uses of the device;

(c) a cam actuator connected to the shank of the cam member and having a handle portion projecting forwardly of the body unit for manipulating the device, the actuator being movable relative to the cam member from an expanding position to a contracting position, the cam member being movable from the first postion to the second position, but not the third position, when the actuator is in the expanding position, the cam member being movable from the second position to the third position when the actuator is in the contracting position, wherein the first position of the cam member is visually distinguishable from the other positions thereof externally of the device, and wherein the body unit has an outside diameter D in the contracted condition and an expansion diameter D' in the expanded condition, D' being at least approximately 10 percent larger than D for holding the body unit sealingly engaged with the penis cavity.

* * * * *